United States Patent
Humblot et al.

(10) Patent No.: US 10,156,516 B2
(45) Date of Patent: Dec. 18, 2018

(54) PORTABLE DEVICE FOR THE IN-LINE MEASUREMENT OF THE HYDROGEN SULFIDE CONCENTRATION OF AN OFF-GAS

(71) Applicant: ARKEMA FRANCE, Colombes (FR)

(72) Inventors: Francis Humblot, Lanneplaa (FR); Paul Guillaume Schmitt, Lescar (FR); Jean-Luc Dubos, Biron (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 15/543,084

(22) PCT Filed: Jan. 26, 2016

(86) PCT No.: PCT/EP2016/051586
§ 371 (c)(1),
(2) Date: Jul. 12, 2017

(87) PCT Pub. No.: WO2016/120277
PCT Pub. Date: Aug. 4, 2016

(65) Prior Publication Data
US 2018/0003625 A1    Jan. 4, 2018

(30) Foreign Application Priority Data
Jan. 27, 2015 (FR) .................... 15 50615

(51) Int. Cl.
*G01N 21/00* (2006.01)
*G01N 21/3504* (2014.01)
(Continued)

(52) U.S. Cl.
CPC ......... *G01N 21/3504* (2013.01); *G01N 21/33* (2013.01); *G01N 21/39* (2013.01);
(Continued)

(58) Field of Classification Search
CPC .... G01N 21/3504; G01N 21/35; G01N 21/39; G01N 33/00; G01N 21/33; G01N 21/31; G01N 33/0031; G01N 33/0044; G01N 33/0006; G01N 21/3103; G01N 2201/024; G01N 2201/06113; G01N 1/22; B01J 8/00; B01J 8/001; C01B 17/04; G01F 25/00; G01F 1/05; B01D 53/58; G05D 7/00; E21B 47/10
See application file for complete search history.

(56) References Cited

U.S. PATENT DOCUMENTS 6,355,150 B1  3/2002 Savin-Poncet et al.
8,071,068 B2  12/2011 Grandjean et al.
(Continued)

FOREIGN PATENT DOCUMENTS

CN  101 782 514 B     9/2011
CN  101782514 B  *  9/2011  .............. G01N 21/39
(Continued)

OTHER PUBLICATIONS

Chen et al., Appl. Phys B, 90:311-15 (2008).
(Continued)

*Primary Examiner* — Jamil Ahmed
(74) *Attorney, Agent, or Firm* — RatnerPrestia

(57) ABSTRACT

The invention relates to a device and to a method for continuously measuring the hydrogen sulfide concentration of an off-gas by means of a detachable device suitable for being temporarily connected to equipment producing the off-gas. The method comprises a step of measuring the absorption of electromagnetic radiation by the off-gas. The device and method method can be used in particular to measure the hydrogen sulfide concentration in an off-gas produced during a step of sulfiding a hydroprocessing catalyst.

14 Claims, 1 Drawing Sheet

(51) Int. Cl.
  *G01N 21/33*  (2006.01)
  *G01N 21/39*  (2006.01)
  *G01N 33/00*  (2006.01)
  *G01N 21/31*  (2006.01)

(52) U.S. Cl.
  CPC ..... *G01N 33/0006* (2013.01); *G01N 33/0031* (2013.01); *G01N 33/0044* (2013.01); *G01N 21/3103* (2013.01); *G01N 2201/024* (2013.01); *G01N 2201/06113* (2013.01)

(56) References Cited

U.S. PATENT DOCUMENTS

| | | | |
|---|---|---|---|
| 8,163,242 B2 | 4/2012 | Elkins | |
| 2014/0271371 A1* | 9/2014 | Robinson | B01J 8/001 422/108 |

FOREIGN PATENT DOCUMENTS

| | | |
|---|---|---|
| CN | 203 595 659 U | 5/2014 |
| FR | 2 778 743 | 11/1999 |
| FR | 2 944 456 | 10/2010 |
| WO | WO 2014/144038 A1 | 9/2014 |

OTHER PUBLICATIONS

Hodgkinson and Tatam, Measurement Science and Technology, 24:1-59 (2013).
International Search Report for International Application No. PCT/EP2016/051586, dated May 17, 2016.
Modugno et al., Optics Communications, 145:76-80 (1998).
Weldon et al., Sensors and Actuators B, 29:101-7 (1995).

* cited by examiner

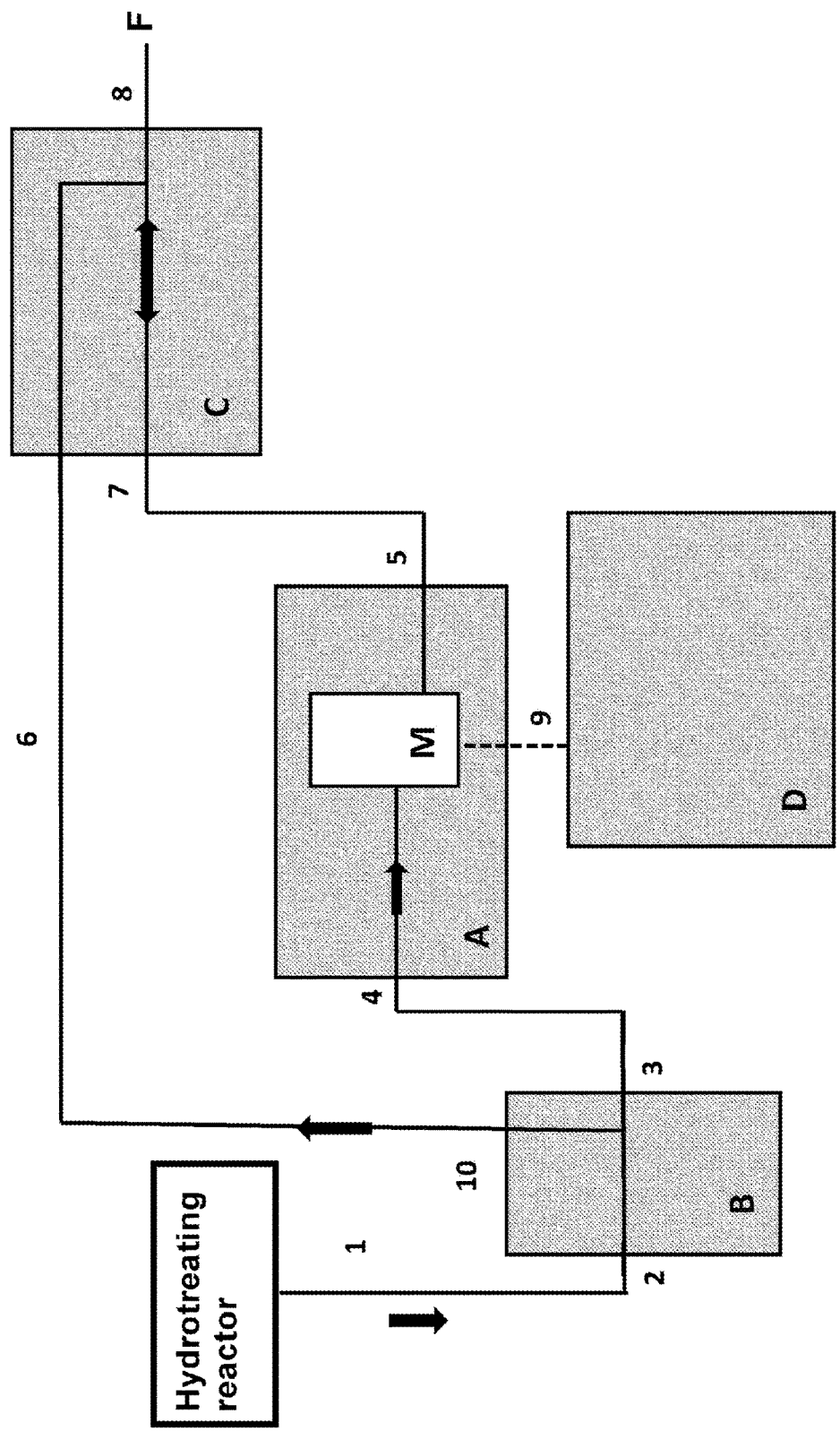

PORTABLE DEVICE FOR THE IN-LINE MEASUREMENT OF THE HYDROGEN SULFIDE CONCENTRATION OF AN OFF-GAS

CROSS-REFERENCE TO RELATED APPLICATIONS

This patent application is a U.S. National Phase Patent Application of PCT Application No. PCT/EP2016/051586, filed Jan. 26, 2016, which claims priority to French Patent Application No. 1550615, filed Jan. 27, 2015, each of which is incorporated by reference herein in its entirety for all purposes.

FIELD OF THE INVENTION

The technical field of the invention is that of the devices and methods used for measuring the concentration of hydrogen sulfide in an off-gas, in particular when the off-gas originates from a reactor used for hydrotreating petroleum products.

BACKGROUND OF THE INVENTION

Hydrotreating is a process used mainly in oil refining, the purpose of which is to remove impurities such as, for example, the sulfur contained in petroleum cuts resulting from the distillation of the crude oil. A hydrotreating unit comprises a reactor comprising two feed ducts, one intended for introducing the petroleum cut and the other intended for introducing pressurized hydrogen. The reactor contains a catalyst which facilitates the conversion of the sulfur-containing compounds to hydrogen sulfide $H_2S$.

In such a process, it is necessary to sulfide the hydrotreating catalyst which is, usually, sold in an inactive form consisting of metal oxides of group 6 metals combined with group 9 and/or 10 metals, these oxides being supported on a porous solid such as, for example, an alumina. This sulfidation operation takes place at each catalyst change and its objective is to convert the metal oxides to sulfides which constitute the active species in the hydrotreating reaction. To do this, it is known to bring the catalyst into contact with a source of sulfur, such as dimethyldisulfide (DMDS). Under the effect of a high temperature and pressure, the dimethyldisulfide breaks down to give hydrogen sulfide that reacts with the catalyst to form the desired metal sulfides. A detection of hydrogen sulfide formed during the sulfidation of the catalyst is necessary since it makes it possible to have an estimate of the degree of progression of the sulfidation reaction. Moreover, it is desirable to minimize the amount of hydrogen sulfide emitted during the sulfidation reaction. In addition, the measurement of the hydrogen sulfide concentration is currently carried out by the refinery staff, at best every hour, under safety conditions which may be dangerous, in particular due to the toxicity of the hydrogen sulfide ($H_2S$). A device and a technique have therefore been sought that enable a reliable, more frequent measurement under increased safety conditions.

Devices exist for on-line measurement of the concentration of hydrogen sulfide in off-gases originating from units that oxidize the hydrogen sulfide to sulfur, known as Claus units. These are for example described in documents FR 2 778 743 and FR 2 944 456. However, these devices are designed to be permanently mounted on the plant producing the effluent containing the hydrogen sulfide. They cannot be easily dismantled in order to be rapidly used on another Claus unit.

Document CN 203595659U describes a device for measuring the concentration of hydrogen sulfide in a gas stream, the operating principle of which is based on a laser spectroscopy analysis. However, this device requires the use of a gas for inerting the laser equipment, that is to say a gas which is not an oxidizer with the gas to be analyzed and which renders the measurement device anti-explosive. However, the use of an inerting gas makes the device complex.

A measurement device is therefore sought that is easily transportable from one site to another and which does not require the use of an inerting gas.

Document U.S. Pat. No. 8,163,242 describes a device for measuring the concentration of chemical species contained in gases derived from the decomposition of waste present in landfills. However, this document gives no information on the technique used for specifically measuring the hydrogen sulfide concentration. Moreover, this measurement device appears to require an electrochemical technique, which is not suitable for measurements of high concentrations without requiring a dilution gas. The analysis equipment from this document is "a chemical analyser", which on principle implies an irreversible chemical reaction, therefore a frequent replacement of the chemical sensors.

Document WO 2014/144038 describes a device for the real-time measurement of the concentration of hydrogen sulfide in a petroleum product hydrotreating unit. This device is transportable and is connected temporarily to the outlet duct of the hydrotreating unit. Preferably, the measurement is based on the chemical reaction that occurs between lead acetate and hydrogen sulfide. Lead acetate is deposited on a paper tape, thus giving the tape a white color. During the chemical reaction, black lead sulfide is formed. The degree of darkness of the paper tape is proportional to the amount of hydrogen sulfide that has passed through the measurement system. This measurement system nevertheless has the following drawbacks:

- It requires a diffusion chamber intended to dilute, for example with nitrogen, the gas for which it is desired to measure the hydrogen sulfide concentration. The dilution gas may either originate from a local network, or be conveyed with the transportable analysis device. The fact of using nitrogen derived from a refinery may lead to analysis errors due to the pollution resulting from the processes carried out in the refinery.
- The replacement of the used paper with new paper impregnated by lead acetate is carried out by an operator. Yet lead acetate belongs to the chemical substances that are carcinogenic and/or mutagenic and/or or toxic for reproduction (so-called CMR substances). Each paper change exposes the operator to contact with lead acetate, which is a health hazard.
- This device does not make it possible to maintain a good accuracy of measurement of the $H_2S$ concentration over time, over a broad concentration range extending from 0 to 30 000 ppm.

This document also indicates that the detection of the hydrogen sulfide may be carried out by an electrochemical method.

Document CN 101782514 discloses a device for measuring the concentration of hydrogen sulfide in a natural gas, before and after desulfurization, this device comprising a portion installed in a fixed manner on a plant in which the gas containing H₂S circulates, and a detachable portion that can be connected to this fixed portion. The fixed portion comprises:
- a measurement chamber wherein the absorption by the gas of a laser radiation is measured;
- a pressure gauge and an expansion valve that make it possible to regulate the pressure of the gas to be analyzed to the working pressure of the measurement chamber.

The detachable portion comprises:
- a device for producing laser radiation; and
- a device that processes the optical signal from the measurement chamber.

This portion is detachable since it can be connected to the fixed portion with the aid of two optical fibers. Consequently, in this document, only the portion dedicated to the production of the laser radiation and to the processing of the signal is detachable.

Therefore, it has long been sought in the prior art to have a transportable device for the accurate continuous measurement of the hydrogen sulfide concentration of an off-gas, generally between 100 ppm and 50 000 ppm by volume, preferably between 100 ppm and 30 000 ppm, which can be connected temporarily to a duct for transporting this off-gas and which does not use dilution gas. Preferably, this device should not require the use of dangerous chemical substances such as, amongst others, CMR (carcinogenic, mutagenic, reprotoxic) substances. More preferably, this device should not require a supply of an inerting gas.

SUMMARY OF THE INVENTION

One subject of the invention is a kit for measuring the hydrogen sulfide concentration of a gas likely to contain it, said kit comprising separate modules that can be connected to one another, said modules being the following:
- a measurement module A comprising a measurement chamber M wherein the absorption by the gas of a monochromatic electromagnetic radiation is measured;
- an expansion module B that makes it possible to bring the pressure of the gas to be analyzed to the working pressure of the measurement module;
- a pressure-regulating module C capable of maintaining the pressure of the gas in the measurement chamber at a value lying within the range of working pressure values of the measurement module;
- a module D for processing the absorption measurement, which makes it possible to obtain the concentration of hydrogen sulfide in the gas, and also
- means which make it possible to connect the modules to one another.

The gas for which it is desired to measure the hydrogen sulfide concentration is generally inflammable.

According to one embodiment, the electromagnetic radiation is a fixed wavelength infrared radiation emitted by a laser, preferably having a wavelength between 780 nm and 3000 nm.

According to one embodiment, the electromagnetic radiation is a monochromatic radiation lying in the ultraviolet or visible wavelength range, preferably in the range of wavelengths between 100 nm and 380 nm, or between 380 and 780 nm, respectively.

According to one embodiment:
- the expansion module B has an inlet duct (2) that receives the gas to be analyzed and an outlet duct (3) connected to an inlet duct (4) of the measurement module A;
- the measurement module A is electrically connected (9) to the processing module D;
- the regulating module C is mechanically connected to the measurement module A (5, 7) and to a duct (8) for discharging the gas out of the kit.

According to one embodiment, the expansion module B makes it possible to bring the pressure of the gas to be analyzed to the working pressure of the measurement module of between 500 hPa (0.5 bar) relative and 2000 hPa (2 bar) relative.

According to one embodiment:
- the measurement module A has a weight of less than or equal to 60 kg, preferably less than or equal to 55 kg, more preferably less than or equal to 50 kg;
- the expansion module B has a weight of less than or equal to 20 kg, preferably less than or equal to 15 kg, more preferably less than or equal to 10 kg;
- the regulating module C has a weight of less than or equal to 20 kg, preferably less than or equal to 15 kg, more preferably less than or equal to 10 kg;
- the processing module D has a weight of less than or equal to 50 kg, preferably less than or equal to 40 kg, more preferably less than or equal to 35 kg.

The kit may be used for measuring the hydrogen sulfide concentration of a gas likely to contain it, said gas comprising at least 50% hydrogen by volume. The gas likely to contain hydrogen sulfide may be an off-gas of a reactor used for the purification of hydrocarbons resulting from refining processes or from petrochemistry.

Another subject of the invention is a method for the continuous measurement of the hydrogen sulfide concentration of an off-gas using a detachable device capable of being connected temporarily to a plant producing said off-gas, the method comprising a step of measuring the absorption by the off-gas of a monochromatic electromagnetic radiation. The measurement method may use the kit as described above, the measurement of the hydrogen sulfide concentration being carried out after mounting the kit on the plant. At the end of the operation, the detachable device may easily be dismantled from the plant and brought back in the form of a kit in order to then be remounted on another plant on which the same type of measurement must be carried out.

According to one embodiment, the electromagnetic radiation is a fixed wavelength infrared radiation emitted by a laser, preferably having a wavelength between 780 nm and 3000 nm.

According to one embodiment, the electromagnetic radiation is a monochromatic radiation lying in the ultraviolet or visible wavelength range, preferably in the range of wavelengths between 100 nm and 380 nm, or between 380 and 780 nm, respectively.

According to one embodiment, the method for the continuous measurement of the hydrogen sulfide concentration of a likely gas comprises the use, as a device, of the kit according to the invention.

According to one embodiment, the gas is an off-gas from a reactor used for the purification, with hydrogen, of hydrocarbons resulting from refining processes or from petrochemistry.

According to one embodiment, the method is used for monitoring the progression and/or ensuring the end of the step of sulfiding a hydrotreating catalyst.

A final subject of the invention is a plant in which a gas stream containing hydrogen sulfide is likely to be generated, characterized in that it integrates a device obtained by the mounting of the kit according to the invention.

BRIEF DESCRIPTION OF THE DRAWING

FIG. 1 schematically represents, according to one embodiment of the invention, the connection of the device according to the invention to the outlet of a hydrotreating unit and also the connections of the various modules to one another.

DETAILED DESCRIPTION OF CERTAIN EMBODIMENTS OF THE INVENTION

The device according to the invention is in the form of a kit comprising separate modules that can be connected to one another, said modules being the following:
- a measurement module A comprising a measurement chamber M wherein the absorption by the gas of an electromagnetic radiation is measured;
- an expansion module B that makes it possible to bring the pressure of the gas to be analyzed to the working pressure of the measurement module;
- a pressure-regulating module C capable of maintaining the pressure of the gas in the measurement chamber at a value lying within the range of working pressure values of the measurement module;
- a module D for processing the absorption measurement, which makes it possible to obtain the concentration of hydrogen sulfide in the gas, and
- means which make it possible to connect the modules to one another.

The description of the arrangement of the various modules of the kit according to one embodiment of the invention is made with reference to FIG. 1.

The measurement module A comprises an inlet duct (4) capable of being mechanically connected to the outlet duct (3) of the expansion module B and an outlet duct (5) capable of being mechanically connected to a duct (7) of the regulating module C. The hydrogen sulfide concentration is measured in a measurement chamber M according to the known principle of spectrophotometry. According to this principle, an electromagnetic radiation passes through a substance and the absorption of this electromagnetic radiation by the substance is measured. This measurement chamber consists of a stainless steel vessel, generally of tubular shape and having a length of between 5 and 80 cm, preferably between 10 and 50 cm. This measurement chamber comprises an electromagnetic radiation-emitting source and a sensor of this radiation that converts the radiation into an electrical signal. The emitting diode and the sensor may be fixed to the walls of the measurement cell opposite one another or side-by-side. In the latter case, the electromagnetic radiation is reflected on a mirror that sends the radiation back to the sensor. This configuration increases the optical path and the sensitivity of the measurement. The choice of one or the other of the configurations depends on the wavelength of the electromagnetic radiation and on its coefficient of absorption of the radiation by the hydrogen sulfide, and also on the hydrogen sulfide concentration measurement range chosen. Optionally, the source of electromagnetic radiation and the sensor may be offset from the measurement chamber by adding two optical fibers in order to bring the electromagnetic radiation from the source to the measurement chamber and to bring back this same radiation, after absorption, to the sensor.

The electromagnetic radiation may be:
- either a laser light emitting in the infrared at a fixed wavelength between 780 and 3000 nm;
- or a monochromatic electromagnetic radiation emitting in the ultraviolet range or the visible range, that is to say in the range of wavelengths between 100 nm and 380 nm, or between 380 and 780 nm, respectively.

Use may be made of an infrared laser analyzer: "SS2100 TDL Gas Analyser" model sold by Spectra Sensor, or a UV-Visible analyzer: "OMA-300 Hydrogen Sulfide Analyzer" model sold by Applied Analytics.

The module A generally has a weight of less than or equal to 60 kg, preferably less than or equal to 55 kg, more preferably less than or equal to 50 kg.

The expansion module B comprises:
- an inlet duct (2) capable of being mechanically connected to the duct (1) itself mounted as a bypass of the outlet duct of the gases from a hydrotreating reactor.
- an outlet duct (3) capable of being mechanically connected to the inlet duct (4) of the measurement module A. Its role is to reduce the pressure of the gas to the working pressure of the measurement module which is generally between 500 hPa and 2000 hPa.
- optionally an outlet duct (10) used to discharge an overpressure not compatible with the working pressure of the measurement module which is generally between 500 hPa and 2000 hPa. It acts as a safety member.

The expansion module B generally has a weight of less than or equal to 20 kg, preferably less than or equal to 15 kg, more preferably less than or equal to 10 kg.

The regulating module C has an inlet duct (6) capable of optionally being mechanically linked to the duct (10) and two ducts (7, 8). One of the two ducts (8) is a duct for discharging the gas or that is used to convey the gas to a gas destruction device, such as a flare for combusting the gas. The other duct (7) is capable of receiving the gas from the measurement module A as gas to be analyzed. The regulating module makes it possible to regulate the pressure in the measurement chamber of the module A to a value lying in the range of working pressures of the measurement module. If the pressure is less than the lower limit of the range of working pressures, the expansion module B sends gas into the measurement chamber through the duct (3). If this pressure exceeds the upper limit of the range of working pressures, gas is injected into the duct (10) then the duct (8) for discharging or destroying the gas. The duct (8) also receives the gas originating from the measurement module A when the latter is operating within its range of working pressure.

The regulating module C generally has a weight of less than or equal to 20 kg, preferably less than or equal to 15 kg, more preferably less than or equal to 10 kg.

The module D for processing the spectroscopic signal is electrically connected to the module B by means of the electrical connection (9). It converts the measurement of the absorption originating from the module A into a hydrogen sulfide concentration. In one preferred embodiment of the invention, the instantaneous hydrogen sulfide content may be indicated by a screen, advantageously integrated into the module D.

The processing module D generally has a weight of less than or equal to 50 kg, preferably less than or equal to 40 kg, more preferably less than or equal to 35 kg.

The analysis results generated by the processing module D may be transferred during or after analysis, completely or partly, to a computer by means of a wireless transmission, for example of Wi-Fi, Bluetooth, etc. type, or a wired transmission by means of a memory card.

The modules A and D may each be contained in a thick metal housing that is explosion-proof in accordance with the 94/9/EC directive, that is to say that a potential explosion remains confined inside the housing which is not damaged.

The off-gas containing the hydrogen sulfide to be analyzed may be derived from a hydrotreating reactor HDT. The off-gas generally contains between 100 and 50 000 ppm by volume of hydrogen sulfide, preferably between 100 and 30 000 ppm by volume, more preferably between 1000 and 20 000 ppm by volume.

At the outlet of the hydrotreating reactor, this hydrogen-rich off-gas is separated from the liquid hydrocarbons in a vessel in which the liquid compounds accumulate at the bottom whilst the non-condensable gases are discharged at the top. These gases are, in general, recompressed by a compressor in order to be reinjected upstream of the hydrotreating reactor or reactors. These gases constitute the off-gas for which it is desired to know the hydrogen sulfide content. For this, a circuit terminated by a connection duct (1) is positioned as a bypass of the main gas stream. This duct (1) is connected to the inlet duct (2) of the module B. The gas to be analyzed is therefore transported into the expansion module B by the inlet duct (2) then is transferred by the outlet duct (3) into the measurement module A comprising the measurement chamber M. It is then sent into the regulating module C. It is discharged from the regulating module C and is sent to the flare (F) in order to be burnt therein. The regulating module C keeps the pressure of the gas in the measurement module at a constant value by adjusting the amount of gas sent into the measurement chamber M and the amount sent to the flare F. Should the gas to be analyzed be, in the duct (1), at a pressure compatible with the working pressure of the measurement module A, the expansion module would be optional. The connections between the modules A, B and C and also those for connecting to the gas sampling point (1) and also to the discharge circuit via the flare F are provided by flexible hoses that can withstand a maximum pressure of 25 MPa. They are equipped with quick couplings and closure members that are designed to be connected and disconnected frequently.

The module D is connected to the module A by electric cables.

According to one embodiment, the modules A and D are integral within one and the same housing to which the modules B and C are connected.

According to one embodiment, the modules A and C are integral within one and the same housing to which the modules B and D are connected.

According to one embodiment, the modules A, C and D are integral within one and the same housing to which the module B is connected.

The device according to the invention may be easily connected without opening of the circuit, which limits the risk of exposure of an operator to hazardous gases.

Within the context of the sulfiding of the hydrotreating catalyst, DMDS is injected at the flow rate requested by the refinery throughout the catalyst activation procedure, which generally lasts from 1 to 2 days, and at the same time as the injection of DMDS, the device according to the invention is used to measure and monitor the increase in the concentration of hydrogen sulfide over time. When the concentration of hydrogen sulfide, compared to the amount of DMDS injected, shows that there is no more sulfur fixed by the catalyst, this means that it is no longer useful to continue to inject DMDS.

The device according to the invention has the following advantages:

a) It can be disconnected from the plant producing the off-gas containing the hydrogen sulfide after the concentration has been measured and it can be rapidly transported to another site in order to be used thereat. The device according to the invention is characterized by the fact that it can easily be transported by truck, airplane, automobile or boat, due to its limited weight (for example 2 modules of less than 50 kg each and 2 modules of less than 10 kg each) and its reduced dimensions, i.e. generally less than 800 mm×600 mm×400 mm. It can also be transported by a person, without this person having to use a handling device.

b) It is "self-contained" in that it does not require the use of any gas, other than the one that is being analyzed. In particular:

It does not require any carrier gas, which represents an advantage relative to the gas chromatography measurement techniques that require the use of hydrogen or helium.

It does not necessarily require the use of an inerting gas to make it comply with the ATEX (ATmosphères EXplosives [explosive atmospheres]) regulations relating to equipment intended to be used in explosive atmospheres.

It does not require the use of a dilution gas, unlike the electrochemical measurement techniques or the measurement techniques that use the reaction between hydrogen sulfide and lead acetate, as mentioned in document WO 2014/144038.

c) It is characterized by a low measurement uncertainty (<100 ppm) over the entire measurement range desired for the hydrotreating application, unlike the techniques that require a dilution gas, such as the one based on the use of a paper impregnated with lead acetate.

d) It enables a continuous analysis of the concentration of hydrogen sulfide, with a measurement frequency lying within the range extending from 5 to 30 seconds depending on the flow rate of the gas to be analyzed. Owing to this continuous measurement, the refiner may react more rapidly to drifts of the hydrogen sulfide content in order to adjust, for example, the DMDS injection flow rate. Thus, high concentrations of hydrogen sulfide, greater than 3% by volume, harmful for the recompression section, and excessively low concentrations, lower than 0.1% which may damage the catalyst when the temperature of the reactor exceeds 250° C., are avoided.

e) It does not require the use of hazardous chemical compounds, such as lead acetate.

f) It complies with the ATEX regulations (European explosion-proof or anti-explosion standard) while being both easily transportable and not very bulky. Specifically, industrial analysis equipment suppliers only offer fixed and bulky equipment that at the very least meets the ATex II 2 G Ex d II B+H2T4 standard. The ATEX classification of equipment is based on European directive 94/9/EC.

The kit according to the invention satisfies point "p" (suppression of the explosive atmosphere) of the ATEX classification and/or point "e" (suppression of the source of combustion) and/or point "d" (explosion-proof, no propagation of combustion). Preferably, the kit according to the invention satisfies at least point "d" of the ATEX classification by the use of explosion-proof housings around the modules A and D.

The description of the invention was given in the foregoing by taking the example of the measurement of the hydrogen sulfide in an off-gas derived from a unit for hydrotreating petroleum cuts. However, the invention is not limited to this application and may be used in oil refining processes in which hydrogen is used to purify hydrocarbons. It may also be used to measure the amount of hydrogen sulfide present in an off-gas derived from a unit carrying out the catalytic oxidation reaction of hydrogen sulfide to give sulfur (Claus reaction). It may also be used in petrochemistry or in processes for converting products of natural origin ("biorefining"). It may also be used in the fields of industry that produce hydrogen sulfide, such as the treatment of wastewater, blast furnaces, papermaking, tanning.

The invention claimed is:

1. A kit for measuring a hydrogen sulfide concentration of a gas having a hydrogen sulfide concentration and wherein the gas comprises at least 50% hydrogen by volume, wherein the kit comprises separate modules that can be connected to one another to provide a detachable device, the modules comprising:
   a measurement module A comprising a measurement chamber M wherein an absorption of a monochromatic electromagnetic radiation by the gas is measured and an absorption measurement related to the hydrogen sulfide concentration is produced, and wherein the measurement chamber M comprises a generally tubular stainless steel vessel having a length of between 5 cm and 80 cm, and wherein the measurement module A has a range of working pressure values, and wherein the measurement module A is contained in a metal housing that is constructed and arranged to be explosion-proof in accordance with European 94/9/EC directive ATEX classification points p and/or e and/or d without the need for an inerting gas;
   an expansion module B that brings the pressure of the gas to the range of working pressure values of the measurement module A, wherein the expansion module B comprises an inlet duct that receives the gas having a hydrogen sulfide concentration and an outlet duct, and wherein the outlet duct of expansion module B is configured to connect to an inlet duct of the measurement module A;
   a pressure-regulating module C that maintains the pressure of the gas in the measurement chamber M at a pressure lying within the range of working pressure values of the measurement module A, wherein the pressure-regulating module C comprises an inlet duct that is configured to mechanically connect to an outlet duct of the measurement module A and the pressure-regulating module C is further configured to connect to a discharge duct that discharges the gas having a hydrogen sulfide concentration out of the detachable device;
   a processing module D that processes the absorption measurement, whereby the concentration of hydrogen sulfide in the gas is determined, wherein the measurement module A is configured to be electrically connected to the processing module D, and wherein the processing module D is contained in a metal housing that is constructed and arranged to be explosion-proof in accordance with European 94/9/EC directive ATEX classification points p and/or e and/or d without the need for an inerting gas.

2. The kit according to claim 1, wherein the electromagnetic radiation is a fixed wavelength infrared radiation emitted by a laser, wherein the wavelength is between 780 nm and 3000 nm.

3. The kit according to claim 1, wherein the electromagnetic radiation is a monochromatic radiation lying in the ultraviolet or visible wavelength range wherein the wavelength of the radiation is between 100 nm and 780 nm.

4. The kit according to claim 1, wherein the expansion module B brings the pressure of the gas having a hydrogen sulfide concentration to between 500 hPa (0.5 bar) relative and 2000 hPa (2 bar) relative.

5. The kit according to claim 1, wherein:
   the measurement module A has a weight of less than or equal to 60 kg;
   the expansion module B has a weight of less than or equal to 20 kg;
   the regulating module C has a weight of less than or equal to 20 kg; and
   the processing module D has a weight of less than or equal to 50 kg.

6. A method for the continuous measurement of a hydrogen sulfide concentration of an off-gas, wherein the method comprises using a detachable device capable of being connected temporarily to a plant producing said off-gas, wherein the detachable device measures an absorption of a monochromatic electromagnetic radiation by the off-gas and wherein the off-gas comprises at least 50% hydrogen by volume and wherein the detachable device is constructed and arranged to be explosion-proof in accordance with European 94/9/EC directive ATEX classification points p and/or e and/or d without the need for an inerting gas.

7. The method according to claim 6, wherein the monochromatic electromagnetic radiation is a fixed wavelength infrared radiation emitted by a laser, wherein the wavelength is between 780 nm and 3000 nm.

8. The method according to claim 6, wherein the monochromatic electromagnetic radiation lies in the ultraviolet or visible wavelength range, wherein the wavelength of the radiation is between 100 nm and 780 nm.

9. A method for the continuous measurement of the hydrogen sulfide concentration of a gas having a hydrogen sulfide concentration, wherein the method comprises using the detachable device provided by the kit according to claim 1 to measure the hydrogen sulfide concentration.

10. The method according to claim 6, wherein the gas having a hydrogen sulfide concentration is an off-gas from a reactor used for the purification, with hydrogen, of hydrocarbons resulting from refining processes or from petrochemistry.

11. The method according to claim 6, wherein the method is used for monitoring progression of or for ensuring the end of a process of sulfiding a hydrotreating catalyst.

12. A plant having a gas stream having a hydrogen sulfide concentration wherein the plant integrates the kit according to claim 1.

13. A method of using the detachable device provided by the kit according to claim 1 for measuring the hydrogen sulfide concentration of a gas having a hydrogen sulfide concentration, wherein the method comprises the steps of:
   a) temporarily attaching the detachable device to a plant that produces the gas having a hydrogen sulfide concentration,
   b) measuring the hydrogen sulfide concentration,
   c) detaching the detachable device from the plant.

14. The method according to claim 13, wherein the plant comprises a reactor used for purification of hydrocarbons resulting from refining processes or from petrochemistry and the gas having a hydrogen sulfide concentration is an off-gas of the reactor used for purification of hydrocarbons resulting from refining processes or from petrochemistry.

* * * * *